United States Patent [19]

Fox et al.

[11] Patent Number: 4,996,292

[45] Date of Patent: Feb. 26, 1991

[54] SELF-SEALING ARTIFICIAL SKIN COMPRISING COPOLY-ALPHA-AMINO ACID

[76] Inventors: Sidney W. Fox, 707 S. Valley Rd., Carbondale, Ill. 62901; Peter R. Bahn, R.R. 1, Box 261, Woodlawn, Ill. 62898

[21] Appl. No.: 373,503

[22] Filed: Jun. 30, 1989

[51] Int. Cl.$^5$ ............................................. C08G 69/10
[52] U.S. Cl. .................... 528/328; 528/330; 528/331
[58] Field of Search ........................ 528/328, 330, 331

[56] References Cited

U.S. PATENT DOCUMENTS

| 4,525,576 | 6/1985 | Hayashi et al. | 528/328 |
| 4,594,409 | 6/1986 | Hayashi et al. | 528/328 |

*Primary Examiner*—Harold D. Anderson
*Attorney, Agent, or Firm*—Peter R. Bahn

[57] ABSTRACT

Thermally polymerized copolyamino acids are used to make a biologically compatible self-sealing skin.

5 Claims, No Drawings

SELF-SEALING ARTIFICIAL SKIN COMPRISING COPOLY-ALPHA-AMINO ACID

FIELD OF THE INVENTION

This invention relates to the field of protein engineering in general, and to the fields of thermal protein engineering and dermatology in particular.

BACKGROUND OF THE INVENTION

It has long been recognized that the skin or integument of multicellular organisms provides an important barrier between internal tissues of such organisms and the planetary environments in which such organisms live. One of the most important properties of biological skin in contrast non-biological skin is that biological skin usually possesses self-sealability whereas non-biological usually does not.

Among the major components of mammalian skins are various types of biologically generated proteins. Biologically generated proteins are copolyamino acids which have been synthesized on cellular ribosomes with amino acid sequences that are directed by nucleic acids.

However, it was discovered previously that thermal proteins can be made simply by heating amino acids together in a flask for several hours (Fox et al., 1958). Such compounds and methods for their preparation are described in U.S. Pat. Nos. 3,052,655 and 3,076,790, by Fox et al.

Thermal copolyamino acids form a class of thermally engineered proteins (TEPs) because they possess amino acid sequences that have not been currently found in nature. They sometimes are referred to as proteinoids to reflect the fact that, although they resemble proteins structurally and functionally, they are produced abiotically in contrast to biologically generated proteins such as collagen, to use just one example. They are also referred to as thermal proteins for the same reason. Organisms do not make proteins by heating amino acids.

Proteinoids, or TEPS, are much easier to make than proteins which are engineered by genetic means or by standard organic synthetic means.

It was previously found that thermal copolyamino acids, upon being heated in aqueous solution and allowed to cool, spontaneously form microspheres approximately one micron in diameter (Fox, 1960). Such microspheres have been found to mimic many of the properties of biological cells.

The object of this invention was to make a self-sealing artificial skin from thermal copolyamino acids, or TEps, that could mimic some of the proerties of biological skins.

SUMMARY OF THE INVENTION

Amino acids were heat-polymerized to yield thermal copolyamino acids, also known as proteinoids or thermally engineered proteins (TEPs). When the TEPs were boiled in hot water and allowed to cool slowly to room temperature in an undisturbed fashion, all of the TEPs tested formed self-sealing artificial skins on the surface of the proteinoid solutions. Such artificial skins could be picked up and layered on the surface of an object by immersing the object in the solution and bringing it out of solution from underneath the artificial skin that had formed on the surface of the TEP solution.

DESCRIPTION OF THE INVENTION

Preparation of Thermal Copolyamino Acids.

Thermal copolyamino acid PB V 5 (1) was prepared as follows. L-Aspartic acid (100 g), L-glutamic acid (100 g), and an equimolar mixture (50 g) of L-alanine, L-arginine, L-cysteine, glycine, L-histidine, L-isoleucine, L-lysine, L-methionine, L-phenylalanine, L-proline, L-serine, L-threonine, L-tryptophan, L-tyrosine, and L-valine, were mixed together and then placed in a flask. The flask containing the amino acid mixture was then heated in an oil bath at 190° C. for 6 hrs. under a nitrogen atmosphere.

Thermal copolyamino acid PB V 5 (2) was prepared in a similar fashion except that 100 g of L-aspartic acid, 100 g of L-glutamic acid, and 100 g of the equimolar basic neutral (BN) amino acid mixture referred to above was used.

Thermal copolyamino acid PB V 5 (3) was prepared in a similar fashion except that 50 g of L-aspartic acid, 50 g of L-glutamic acid, 50 g of BN mix, and 50 g of L-lysine hydrochloride was used.

Thermal copolyamino acid PB V 5 (4) was prepared in a similar fashion except that 50 g of L-aspartic acid, 50 g of L-glutamic acid, 50 g of BN mix, and 100 g of L-lysine hydrochloride was used and the flask was heated at 195° C. instead of 190° C.

For the sake of convenience, the PB V 5 (1) thermal copolyamino acid is also referred to as a 2:2:1 Asp:Glu:BN TEP, the PB V 5 (2) thermal copolyamino acid is referred to as a 1:1:1 Asp:Glu:BN TEP, the PB V 5 (3) thermal copolyamino acid is referred to as a 1:1:1:1 Asp:Glu:BN:Lys TEP, and the PB V 5 (4) thermal copolyamino acid is referred to as a 1:1:1:2 Asp:Glu:BN:Lys TEP.

Distilled water (1000 ml) was poured into each flask of the resulting glass-like materials. The flasks were stirred overnight. The thermal copolyamino acid mixtures were filtered with Buchner funnels and filter papers. Powdery insoluble fractions of the thermal copolyamino acids were retained by the filter papers. These water-insoluble fractions were left to air dry overnight. The 2:2:1 Asp:Glu:BN TEP and the 1:1:1 Asp:Glu:BN TEP were further dried under a vacuum for another night. The resulting yields of the various TEPs were: 75 g of 2:2:1 TEP, 11 g of 1:1:1 TEP, 11 g of 1:1:1:1 TEP, and 11 g of 1:1:1:2 TEP. With regard to the 1:1:1 TEP, the yield is lower than expected because some of the 1:1:1 preparation formed a tar-like liquid upon addition of water. This was discarded along with the soluble fraction.

Preparation of Self-Sealing Artificial Skins.

Distilled water (1500 ml) was added to each of the water-insoluble TEP fractions (1.5 g–6.0 g) in 2000 ml beakers. The beakers were heated over a large Bunsen burner until the contents were vigorously boiling. At this point, sticky portions of the TEPs adhered to the sides of the beakers. These portions were discarded. The hot colored soutions were decanted into a second set of 2000 ml beakers. Then the hot solutions were poured into 8 in. by 8 in. square Pyrex baking dishes (500 ml per dish). The dishes were allowed to cool slowly to room temperature without being disturbed.

Results. After 24 hours, a dry artificial skin comprised of the various thermal copolyamino acids referred to previously formed on the surface of the solutions in the square Pyrex baking dishes. The TEP skins possessed the ability to self-seal themselves approximately 24 hours after holes of approximately 1-2 cm diamter had been deliberately made in the artificial TEP skins.

Properties of the Self-Sealing Artificial Skins. The TEP skins can be picked up and applied to the surface of any object which is placed in the TEP solution and gently lifted out of the TEP solution from underneath the surface of the TEP skin. The skin thereupon dries on the surface of the subject object. This procedure can be repeated a number of times to build up several laminate layers of the skin upon a subject object. It was also found that the thickness of the skin which forms upon the surface of the TEP solutions is proportional to the concentration of proteinoid used in the preparation of the hot TEP solution.

The self-sealing artificial TEP skins can be applied to any surface where a dry, biologically compatible surface barrier against foreign matter is desired. Such undesirable foreign matter includes dust, dirt, and microbes. Artificial skins of this type have many applications, among them the dressing of mammalian burn wounds.

What is claimed is:

1. A self-sealing artificial skin consisting of copolyamino acids thermally polymerized from a mixture of the following alpha amino acids: aspartic acid, glutamic acid, lysine, alanine, arginine cysteine, glycine, histidine, isoleucine, methionine, phenylalanine, proline, serine, threonine, tryptophan, tyrosine, and valine.

2. A self-sealing artificial skin as described in claim 1 wherein the said copolyamino acids were thermally polymerized from a mixture of the following alpha amino acids: 2 parts aspartic acid, 2 parts glutamic acid, and 1 part an equimolar mixture of alanine, arginine, cysteine, glycine, histidine, isoleucine, lysine, methionine, phenylalanine, proline, serine, threonine, tryptophan, tyrosine, and valine.

3. A self-sealing artificial skin as described in claim 1 wherein the said copolyamino acids were thermally polymerized from a mixture of the following alpha amino acids: 1 part aspartic acid, 1 part glutamic acid, and 1 part an equimolar mixture of alanine, arginine, cysteine, glycine, histidine, isoleucine, lysine, methionine, phenylalanine, proline, serine, threonine, tryptophan, tyrosine, and valine.

4. A self-sealing artificial skin as described in claim 1 wherein the said copolyamino acids were thermally polymerized from a mixture of the following alpha amino acids: 1 part aspartic acid, 1 part glutamic acid, and 1 part an equimolar mixture of alanine, arginine, cysteine, glycine, histidine, isoleucine, lysine, methionine, phenylalanine, proline, serine, threonine, tryptophan, tyrosine, and valine, and 1 part lysine hydrochloride.

5. A self-sealing artificial skin as described in claim 1 wherein the said copolyamino acids were thermally polymerized from a mixture of the following alpha amino acids: 1 part aspartic acid, 1 part glutamic acid, and 1 part an equimolar mixture of alanine, arginine, cysteine, glycine, histidine, isoleucine, lysine, methionine, phenylalanine, proline, serine, threonine, tryptophan, tyrosine, and valine, and 2 parts lysine hydrochloride.

* * * * *